(12) United States Patent
Dolecki et al.

(10) Patent No.: US 10,963,146 B2
(45) Date of Patent: Mar. 30, 2021

(54) USER INTERFACE FOR A SLEEP SYSTEM

(71) Applicant: BOSE CORPORATION, Framingham, MA (US)

(72) Inventors: Eric Dolecki, Holliston, MA (US); Laura Ware, Boston, MA (US); Jonathan Freed, Milton, MA (US); Jack Read, Bolton, MA (US); Debra Reich, Arlington, MA (US); Leela Keshavan, Westborough, MA (US); Brian David Mulcahey, Sudbury, MA (US)

(73) Assignee: BOSE CORPORATION, Framingham, MA (US)

( * ) Notice: Subject to any disclaimer, the term of this patent is extended or adjusted under 35 U.S.C. 154(b) by 386 days.

(21) Appl. No.: 15/267,858

(22) Filed: Sep. 16, 2016

(65) Prior Publication Data
US 2018/0081527 A1    Mar. 22, 2018

(51) Int. Cl.
*G06F 3/0484* (2013.01)
*A61B 5/11* (2006.01)
(Continued)

(52) U.S. Cl.
CPC .......... *G06F 3/04847* (2013.01); *A61B 5/002* (2013.01); *A61B 5/0004* (2013.01);
(Continued)

(58) Field of Classification Search
CPC ...... G06F 3/04847; G06F 3/016; G06F 3/011; G06F 3/015; G06F 19/00; G06F 3/04817; G06F 3/0482; G06F 17/30764; A61B 5/7435; A61B 5/1113; A61B 5/746; A61B 5/743; A61B 5/7475; A61B 2560/0242;
(Continued)

(56) References Cited

U.S. PATENT DOCUMENTS 4,228,806 A    10/1980  Lidow
4,377,345 A *   3/1983  Yamada ............... G04G 13/023
                                                    368/245
(Continued)

FOREIGN PATENT DOCUMENTS

CN    103519784 B    11/2015
CN    105142515 A    12/2015
(Continued)

OTHER PUBLICATIONS

International Search Report and Written Opinion for application No. PCT/US2017/051599 dated Jul. 6, 2018.
(Continued)

*Primary Examiner* — Tuyetlien T Tran
(74) *Attorney, Agent, or Firm* — Lando & Anastasi, LLP

(57) ABSTRACT

A user controllable sleep system is provided-for, including at least one biometric sensor, a processor, memory in communication with the processor, a display in communication with the processor, and a user interface. The user interface provides landscape graphics relating to a selected soundscape comprising one or more related sounds. The user interface also has health indicia indicating health information from the biometric sensor and environmental indicia indicating environmental information received by the processor.

8 Claims, 13 Drawing Sheets

(51) Int. Cl.
| | |
|---|---|
| *G08C 17/00* | (2006.01) |
| *G06F 1/3231* | (2019.01) |
| *A61B 5/00* | (2006.01) |
| *G06F 3/01* | (2006.01) |
| *A61B 5/0205* | (2006.01) |
| *G06F 3/0481* | (2013.01) |
| *G06F 3/0482* | (2013.01) |
| *A61B 5/024* | (2006.01) |
| *A61B 5/08* | (2006.01) |

(52) U.S. Cl.
CPC .......... *A61B 5/0205* (2013.01); *A61B 5/1113* (2013.01); *A61B 5/743* (2013.01); *A61B 5/746* (2013.01); *A61B 5/7435* (2013.01); *A61B 5/7475* (2013.01); *G06F 1/3231* (2013.01); *G06F 3/011* (2013.01); *G06F 3/015* (2013.01); *G06F 3/016* (2013.01); *G06F 3/0482* (2013.01); *G06F 3/04817* (2013.01); *G08C 17/00* (2013.01); *A61B 5/024* (2013.01); *A61B 5/0816* (2013.01); *A61B 2560/0242* (2013.01)

(58) Field of Classification Search
CPC . A61B 5/0816; A61B 5/024; A61B 2560/029; A61B 5/7278; A61B 5/7405; G08C 17/00; A61M 21/00; A61M 2021/0027; A61M 2021/0083; A61M 2205/3592; A61M 2230/63; A61M 2021/0044; A61M 21/02; A61M 2205/18; A61M 2205/502; A61M 2205/505; A61M 2205/52; G04G 11/00; G04G 13/021; G04G 13/02; G04G 13/026; G04G 15/00; G04G 15/003; G04G 21/025; G08B 21/0461; G08B 21/0211
See application file for complete search history.

(56) References Cited

U.S. PATENT DOCUMENTS

| | | | |
|---|---|---|---|
| 5,671,733 A | 9/1997 | Raviv et al. | |
| 5,781,640 A | 7/1998 | Nicolino, Jr. | |
| 5,928,133 A * | 7/1999 | Halyak | A61B 5/02 340/575 |
| 6,236,622 B1 * | 5/2001 | Blackman | G04B 47/00 362/253 |
| 6,662,032 B1 | 12/2003 | Gavish et al. | |
| 6,825,769 B2 | 11/2004 | Colmenarez et al. | |
| 6,888,779 B2 | 5/2005 | Mollicone et al. | |
| 7,248,915 B2 | 7/2007 | Ronnholm | |
| 7,637,859 B2 | 12/2009 | Lindback et al. | |
| 7,850,619 B2 | 12/2010 | Gavish et al. | |
| 8,243,937 B2 | 8/2012 | Nicolino, Jr. et al. | |
| 8,280,067 B2 | 10/2012 | Nicolino, Jr. et al. | |
| 8,280,068 B2 | 10/2012 | Nicolino, Jr. et al. | |
| 8,285,344 B2 | 10/2012 | Kahn et al. | |
| 8,379,870 B2 | 2/2013 | Nicolino, Jr. et al. | |
| 8,485,982 B2 | 7/2013 | Gavish et al. | |
| 8,550,978 B2 | 10/2013 | Ullmann | |
| 8,562,526 B2 | 10/2013 | Heneghan et al. | |
| 8,585,607 B2 | 11/2013 | Klap et al. | |
| 8,731,646 B2 | 5/2014 | Halperin et al. | |
| 8,855,334 B1 * | 10/2014 | Lavine | H04M 19/04 381/119 |
| 8,870,764 B2 | 10/2014 | Rubin | |
| 8,870,785 B2 | 10/2014 | Muehlsteff et al. | |
| 8,964,997 B2 | 2/2015 | Gauger, Jr. | |
| 8,992,434 B2 | 3/2015 | Halperin et al. | |
| 9,072,437 B2 | 7/2015 | Paalasmaa | |
| 9,192,326 B2 | 11/2015 | Kahn et al. | |
| 9,192,333 B1 | 11/2015 | Hayes et al. | |
| 2002/0080035 A1 | 6/2002 | Youdenko | |
| 2002/0186618 A1 * | 12/2002 | Kirkpatrick | G04G 13/021 368/11 |
| 2003/0095476 A1 * | 5/2003 | Mollicone | H05B 47/16 368/250 |
| 2003/0142591 A1 * | 7/2003 | Baweja | G04G 13/023 368/263 |
| 2005/0152223 A1 * | 7/2005 | Kawakami | G04G 13/021 368/12 |
| 2006/0017558 A1 | 1/2006 | Albert et al. | |
| 2006/0102171 A1 | 5/2006 | Gavish | |
| 2007/0055115 A1 | 3/2007 | Kwok et al. | |
| 2007/0083079 A1 | 4/2007 | Lee et al. | |
| 2007/0249952 A1 | 10/2007 | Rubin et al. | |
| 2008/0157956 A1 | 7/2008 | Radivojevic et al. | |
| 2009/0231964 A1 * | 9/2009 | Kraft | G04G 13/02 368/250 |
| 2009/0287109 A1 | 11/2009 | Ferren et al. | |
| 2009/0292222 A1 | 11/2009 | Ferren et al. | |
| 2010/0039399 A1 * | 2/2010 | Kim | G06F 3/0482 345/173 |
| 2010/0087701 A1 | 4/2010 | Berka et al. | |
| 2010/0162169 A1 * | 6/2010 | Skarp | H04M 1/72583 715/833 |
| 2010/0222640 A1 * | 9/2010 | Anderson | G10H 1/26 600/28 |
| 2010/0226212 A1 | 9/2010 | Gobindram | |
| 2010/0281982 A1 | 11/2010 | Liao | |
| 2011/0004047 A1 | 1/2011 | Braspenning et al. | |
| 2011/0144455 A1 | 6/2011 | Young et al. | |
| 2011/0224510 A1 | 9/2011 | Oakhill | |
| 2011/0230790 A1 | 9/2011 | Kozlov | |
| 2011/0257772 A1 * | 10/2011 | Kerber | H04H 20/38 700/94 |
| 2011/0264164 A1 | 10/2011 | Christopherson et al. | |
| 2012/0092171 A1 | 4/2012 | Hwang et al. | |
| 2012/0327748 A1 | 12/2012 | Lee | |
| 2013/0163394 A1 | 6/2013 | Loree, IV | |
| 2013/0234823 A1 * | 9/2013 | Kahn | A61M 21/02 340/3.1 |
| 2013/0289419 A1 | 10/2013 | Berezhnyy et al. | |
| 2013/0289431 A1 | 10/2013 | Gavish et al. | |
| 2013/0338446 A1 | 12/2013 | Van Vugt et al. | |
| 2014/0088373 A1 | 3/2014 | Phillips et al. | |
| 2014/0334645 A1 | 11/2014 | Yun et al. | |
| 2014/0371547 A1 | 12/2014 | Gartenberg et al. | |
| 2014/0371635 A1 | 12/2014 | Shinar et al. | |
| 2015/0141852 A1 | 5/2015 | Dusanter et al. | |
| 2015/0164238 A1 | 6/2015 | Benson et al. | |
| 2015/0173671 A1 | 6/2015 | Paalasmaa et al. | |
| 2015/0230750 A1 | 8/2015 | McDarby et al. | |
| 2015/0258301 A1 | 9/2015 | Trivedi et al. | |
| 2015/0263688 A1 | 9/2015 | Nicolino, Jr. et al. | |
| 2015/0265212 A1 | 9/2015 | Bruekers et al. | |
| 2015/0320354 A1 | 11/2015 | Oakhill | |
| 2015/0320588 A1 | 11/2015 | Connor | |
| 2015/0348390 A1 * | 12/2015 | Berezhnyy | G04G 11/00 340/309.7 |
| 2015/0367097 A1 | 12/2015 | Gavish | |
| 2015/0382123 A1 * | 12/2015 | Jobani | G06F 30/00 700/98 |
| 2016/0015315 A1 | 1/2016 | Auphan et al. | |
| 2016/0055842 A1 | 2/2016 | DeFranks et al. | |
| 2016/0058428 A1 | 3/2016 | Shinar et al. | |
| 2016/0151603 A1 | 6/2016 | Shouldice et al. | |
| 2016/0163181 A1 * | 6/2016 | Levy | G04G 13/02 340/539.13 |
| 2016/0165038 A1 * | 6/2016 | Lim | H04M 1/72566 715/728 |
| 2016/0173943 A1 * | 6/2016 | Roberts | H04N 21/6125 725/110 |
| 2016/0217672 A1 | 7/2016 | Yoon et al. | |
| 2016/0270718 A1 | 9/2016 | Heneghan et al. | |
| 2016/0335886 A1 * | 11/2016 | Wei | G08C 17/02 |
| 2017/0039045 A1 | 2/2017 | Abrahami et al. | |
| 2017/0087330 A1 | 3/2017 | Kahn et al. | |
| 2018/0078197 A1 | 3/2018 | Ware et al. | |
| 2018/0078198 A1 | 3/2018 | Reich et al. | |
| 2018/0078732 A1 | 3/2018 | Keshavan et al. | |

(56) References Cited

U.S. PATENT DOCUMENTS

| | | |
|---|---|---|
| 2018/0078733 A1 | 3/2018 | Freed et al. |
| 2018/0081527 A1 | 3/2018 | Dolecki et al. |
| 2018/0082550 A1 | 3/2018 | Read et al. |

FOREIGN PATENT DOCUMENTS

| | | | | |
|---|---|---|---|---|
| CN | 105231997 A | 1/2016 | | |
| EP | 2278507 A2 | 1/2011 | | |
| EP | 2976993 A2 | 1/2016 | | |
| FR | 2820230 A1 * | 8/2002 | ............ | A61M 21/00 |
| JP | 2007244597 A | 9/2007 | | |
| WO | 2005084538 A1 | 9/2005 | | |
| WO | 2012051630 A2 | 4/2012 | | |
| WO | 2013093712 A1 | 6/2013 | | |
| WO | 2013134160 A2 | 9/2013 | | |
| WO | 2015006364 A2 | 1/2015 | | |
| WO | 2015008285 A1 | 1/2015 | | |
| WO | 2015061579 A1 | 4/2015 | | |
| WO | 2016035073 A1 | 3/2016 | | |
| WO | 2016122143 A1 | 8/2016 | | |
| WO | 2016142793 A1 | 9/2016 | | |

OTHER PUBLICATIONS

Android Headlines: "Samsung Galaxy S5—How to Set an Alarm", YouTube, Apr. 28, 2014, pp. 1-3, XP054978390, Retrieved from the Internet: URL:https://www.youtube.com/watch?v=d8MT5Y5US18.
Communication Relating to Results of the Partial International Search Report for application No. PCT/US2017/051599 dated Dec. 14, 2017.

* cited by examiner

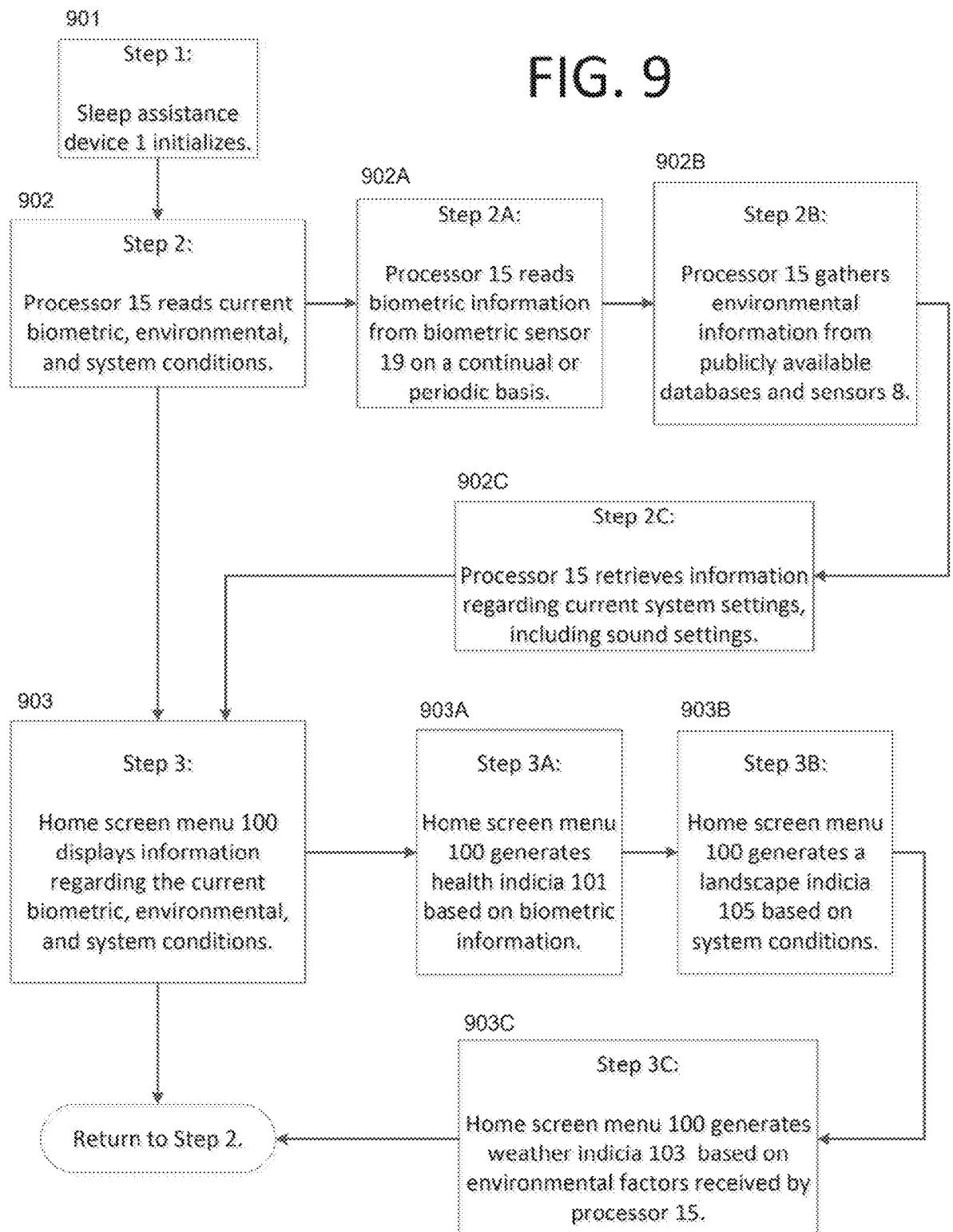

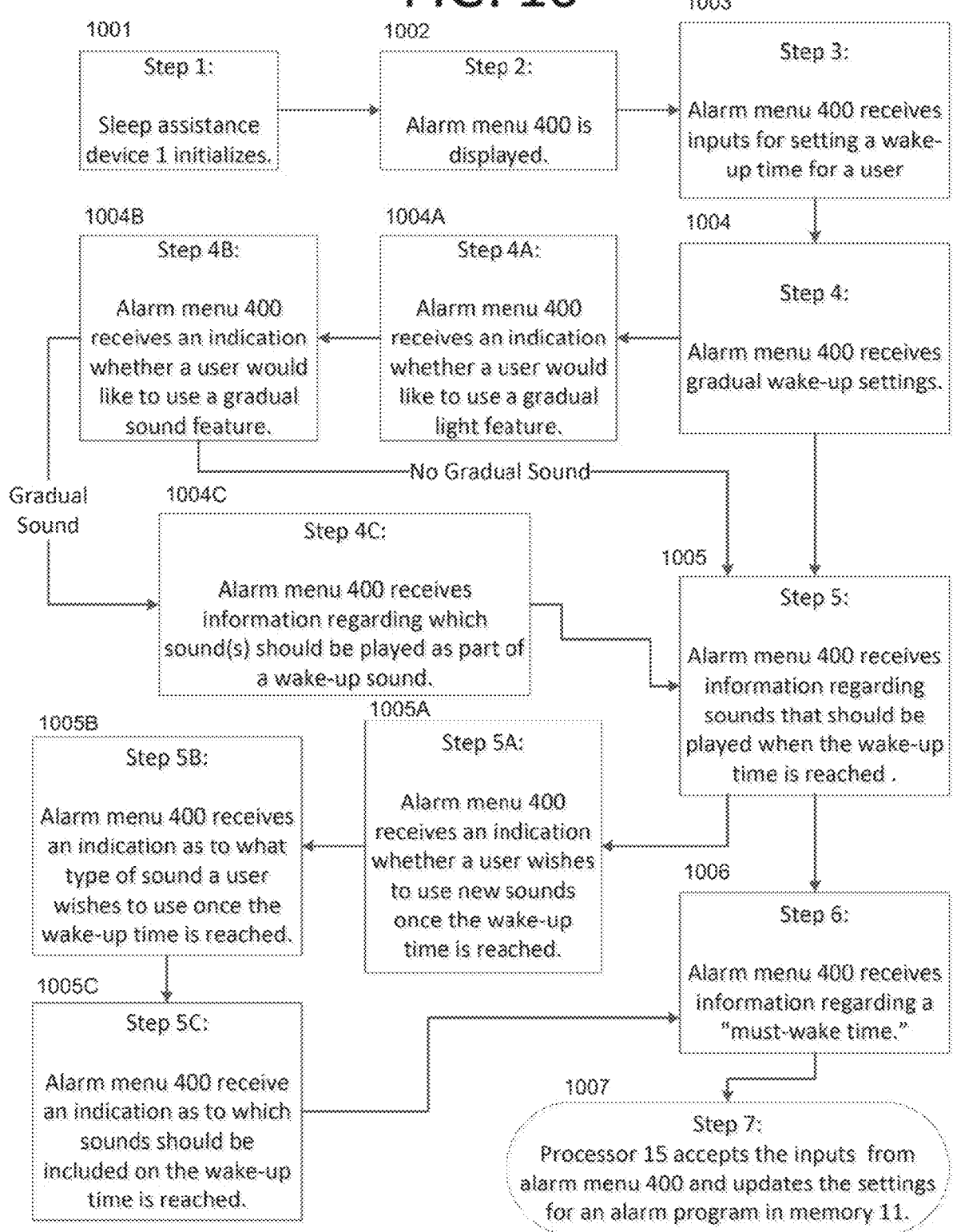

USER INTERFACE FOR A SLEEP SYSTEM

CROSS-REFERENCE TO RELATED APPLICATIONS

This application relates to U.S. patent application Ser. No. 15/267,464 entitled Sleep Quality Scoring and Improvement; U.S. patent application Ser. No. 15/267,552 entitled Intelligent Wake-Up System; U.S. patent application Ser. No. 15/267,567 entitled Sleep Assistance Device; U.S. patent application Ser. No. 15/267,848 entitled Sleep System; and to U.S. patent application Ser. No. 15/267,886 entitled Sleep Assessment Using a Home Sleep System; all of which are filed on even date herewith and are incorporated herein by reference.

FIELD

This disclosure relates to a visual user interface for a user to control and receive information from a sleep system.

BACKGROUND

Sleeplessness and poor or interrupted sleep may significantly affect a person's health. Poor sleep may be caused by such factors as ambient noise, stress, medical conditions, or discomfort. Sleep systems may aid a user in falling to sleep based on settings received from a user. Thus, there exists a need for a device that can provide a user an easy way to control and receive information from a sleep system through the use of a novel visual user interface.

SUMMARY

In one example, a user controllable sleep system is provided-for, including a biometric sensor for sensing at least one of a heart rate, a respiratory rate, a presence of a user, or a movement of a user, the biometric sensor providing output data; a processor; memory in communication with the processor; a display in communication with the processor; and a user interface. The user interface provides landscape graphics relating to a selected soundscape comprising one or more related sounds. The user interface also has health indicia indicating health information from the biometric sensor and environmental indicia indicating environmental information received by the processor. In some examples of the user controllable sleep system, the health indicia represent at least one of a user's respiratory rate or heart rate. In other examples, the user interface is configured to animate the health indicia to provide an indication of information received from the biometric sensor. In some implementations, the user interface is configured to animate the health indicia to provide an indication of at least one of a user's heart rate or respiration. In other implementations, the landscape graphics depict the type of location associated with a soundscape selected by a user. The health indicia may also relate to the location associated with a soundscape selected by a user.

In other examples of the user controllable sleep system, environmental indicia indicate at least one of weather, pollution, pollen, or traffic conditions. The processor may also be configured to retrieve at least one of weather, pollution, pollen, or traffic conditions via a network-accessible database.

A sleep assistance device may also be provided-for, including at least one biometric sensor for sensing at least one of a heart rate, a respiratory rate, a presence of a user, or a movement of a user, each of the at least one biometric sensor providing output data; a processor, memory in communication with the processor, a display in communication with the processor, and speakers in communication with said processor. The processor may be configured to provide a user interface, wherein the user interface presents selectable sound indicia relating to a playable soundscape comprising a plurality of related sounds and the sound indicia control individual sounds that are playable as part of said soundscape. The processor may also be configured to receive a selection of at least one sound indicia and to arrange and play a soundscape based on said selection of at least one sound indicia.

In some examples of the sleep assistance device, the user interface further includes a selectable button for indicating that the processor should automatically execute a relaxation program and at least one selectable button for selecting a triggering event for executing said relaxation program. The at least one selectable button for selecting a triggering event includes at least one of a button for selecting a change in light levels as a triggering event or a button for selecting a user's presence in bed as a triggering event. The user interface further may also include a selectable button for requiring a delay after a triggering event before executing a relaxation program and a slider for indicating the duration of said delay. In other examples, the user interface may also include at least one selectable sound indicia relating to a relaxation program and at least one selectable sound indicia relating to a sound-masking program.

In some examples, the selectable sound indicia includes a selectable preview button for previewing the sounds associated with the selectable sound indicia, one or more images related to the sounds associated the selectable sound indicia, a selectable edge for selecting the sound indicia for inclusion within a soundscape, and an activation status icon for indicating that the selectable sound indicia has been selected for inclusion within a soundscape.

An intelligent alarm is also provided for, including at least one biometric sensor for sensing at least one of a heart rate, a respiratory rate, a presence of a user, or a movement of a user, each of the at least one biometric sensor providing output data; a processor; memory in communication with the processor; a display in communication with the processor; and speakers in communication with the processor. The processor may be configured to provide a user interface, wherein the user interface presents selectable inputs for configuring a wake-up time, selectable inputs for configuring gentle wake-up settings, selectable inputs for configuring alarm time settings, and selectable inputs for configuring a must-wake time. In some examples, the selectable inputs for configuring gentle wake-up settings include a selectable button for selecting a gradual sound feature and selectable sound indicia for selecting sounds to be played as part of a gradual sound feature.

In some examples of the intelligent alarm, the inputs for configuring gentle wake-up settings further includes a selectable button for selecting a gradual light feature. The selectable sound indicia may also include a selectable preview button for previewing the sounds associated with the selectable sound indicia, one or more images related to the sounds associated the selectable sound indicia, a selectable edge for selecting the sound indicia for inclusion within a soundscape, and an activation status icon for indicating that the selectable sound indicia has been selected. In other examples, the selectable inputs for inputting alarm time settings includes buttons for selecting the type of sound to be used as an alarm including at least one of a wake-up chime or a wake-up soundscape, and selectable sound indicia for selecting sounds to be played as part of a wake-up soundscape.

In other examples of the intelligent alarm, the selectable sound indicia includes a selectable preview button for previewing the sounds associated with the selectable sound indicia, one or more images related to the sounds associated the selectable sound indicia, a selectable edge for selecting the sound indicia for inclusion within a soundscape, and an activation status icon for indicating that the selectable sound indicia has been selected. The selectable inputs for defining a must-wake time may also include a selectable button for activating a must-wake time feature, whereby a snooze feature is deactivated upon reaching a must-wake time, and a slider for setting a must-wake time based on an amount of elapsed time after said wake-up time has passed.

BRIEF DESCRIPTION OF THE DRAWINGS

Various aspects of at least one implementation of a visual user interface for a user to control a sleep system are discussed below with reference to the accompanying figures. The figures are provided for the purposes of illustration and explanation and are not intended as a definition of the limits of the disclosure.

FIG. 9 is a flowchart showing a series of steps for a method for providing information on a user interface of a sleep assistance device in one example of the present disclosure.

FIG. 10 is a flowchart showing a series of steps for a method for controlling an intelligent alarm program in one example of the present disclosure.

DETAILED DESCRIPTION

It should be understood that the following descriptions are not intended to limit the disclosure to an exemplary implementation. To the contrary, it is intended to cover alternatives, modifications, and equivalents as may be included within the spirit and scope of the described subject matter.

The present disclosure provides a user interface for a sleep assistance device, a sleep system, and a method of controlling a sleep system through a user interface. At least one biometric sensor senses a heart rate, heart rate variability, a respiratory rate, a presence, or movements of a user, each of the at least one biometric sensor providing output data. The biometric sensor is in communication with a processor and a computer readable memory or other storage component of the sleep assistance device. The present disclosure provides a user interface that allows a user to control a sound program, including a wind-down routine or a sound-masking routine as disclosed, for example, in U.S. patent application Ser. No. 15/267,567, the disclosures of which are hereby incorporated by reference. The present disclosure also provides a user interface for controlling an intelligent alarm, such as the intelligent wake-up system disclosed in U.S. patent application Ser. No. 15/267,552, which is incorporated herein by reference in its entirety. The present disclosure also provides for a user interface for viewing information regarding the quality of a user's sleep, including a sleep score for a user based on observations received from the biometric sensor(s) as disclosed, for example, in U.S. patent application Ser. No. 15/267,464, the disclosures of which are hereby incorporated by reference in their entirety.

Figure 1A:
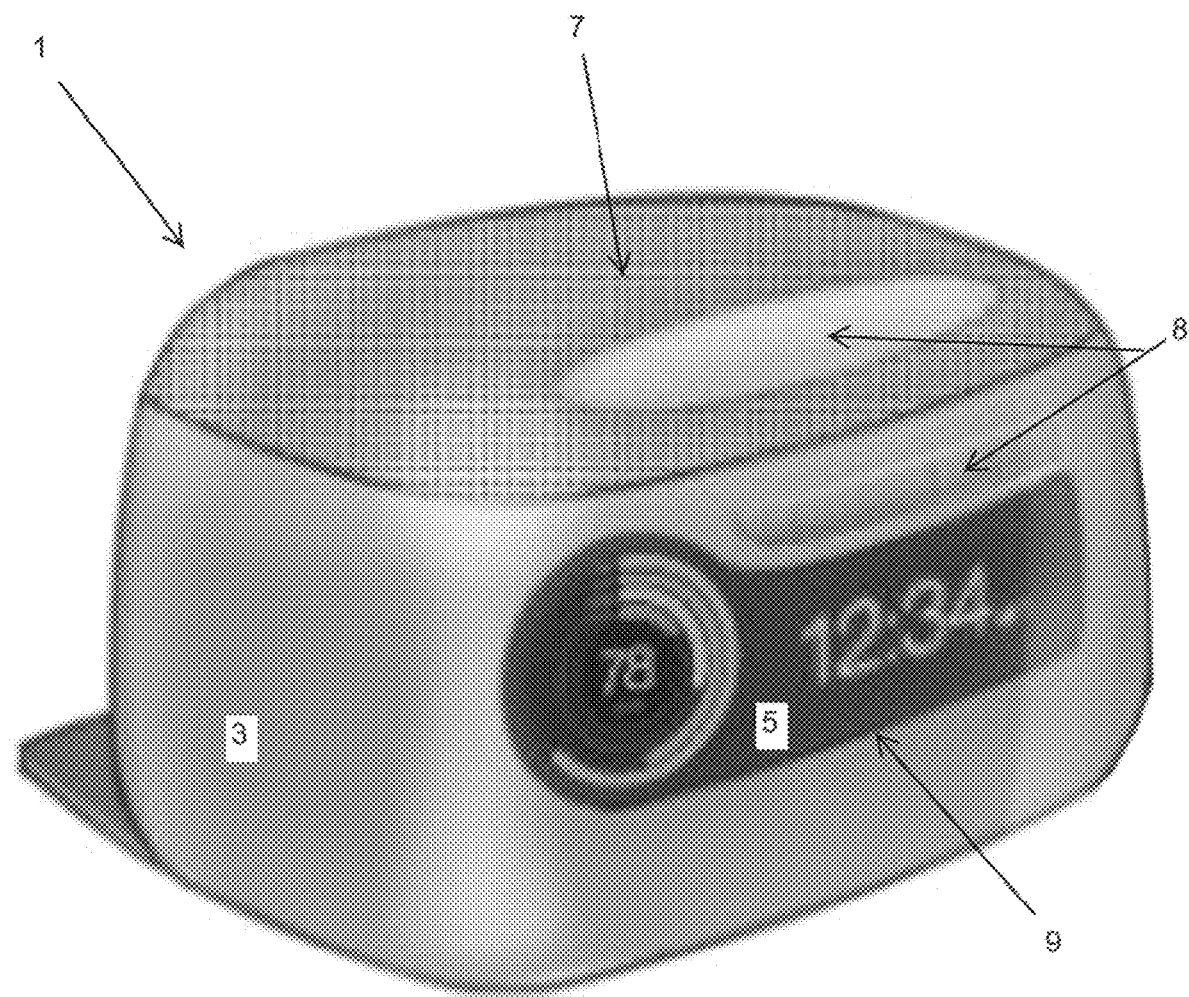
FIG. 1A is a front perspective view of a sleep quality scoring and improvement device with a rectangular housing in one example of the present disclosure.
Figure 1B:
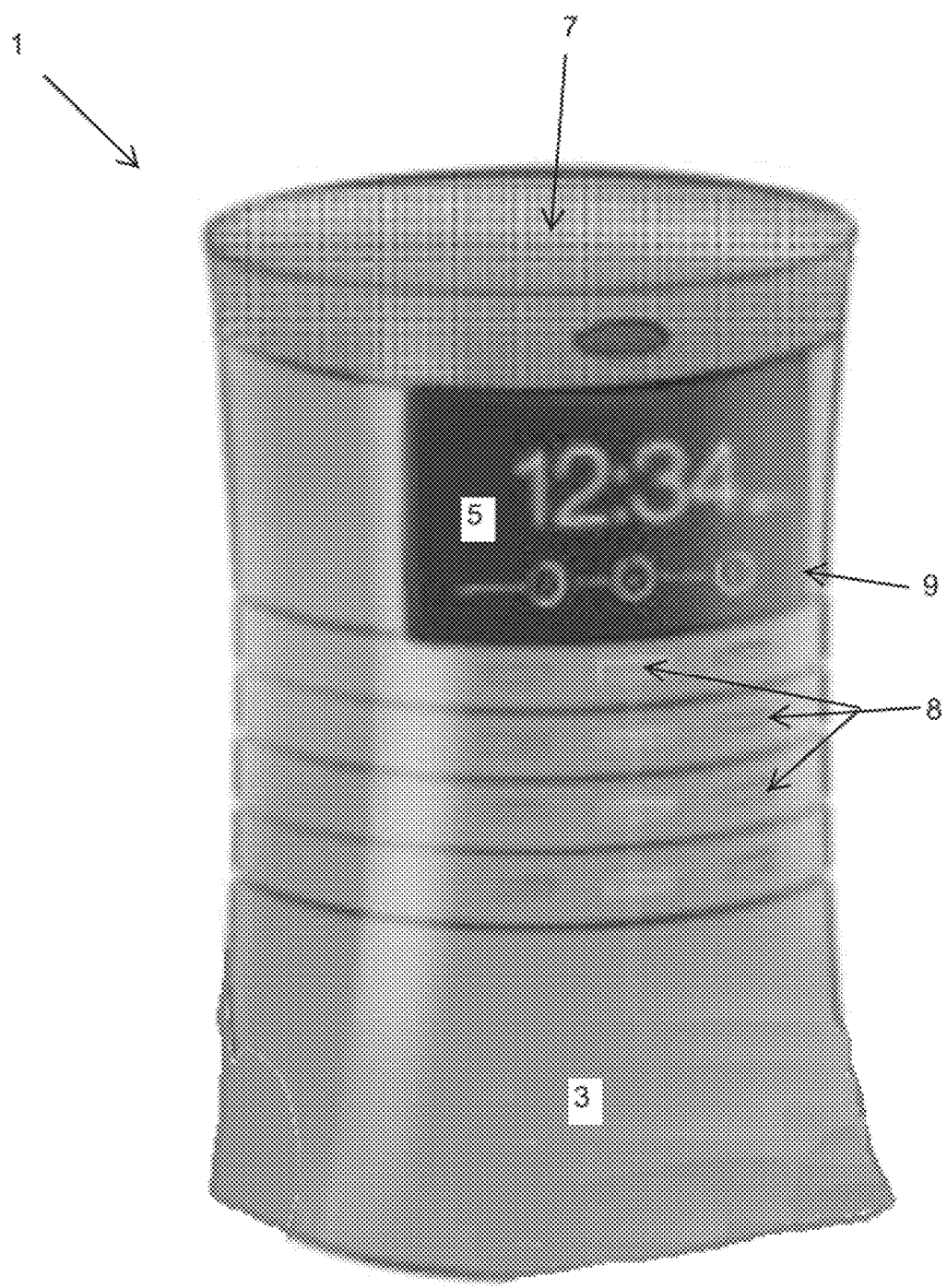
FIG. 1B is a front perspective view of a sleep quality scoring and improvement device with a cylindrical housing in one example of the present disclosure.
Figure 1C:
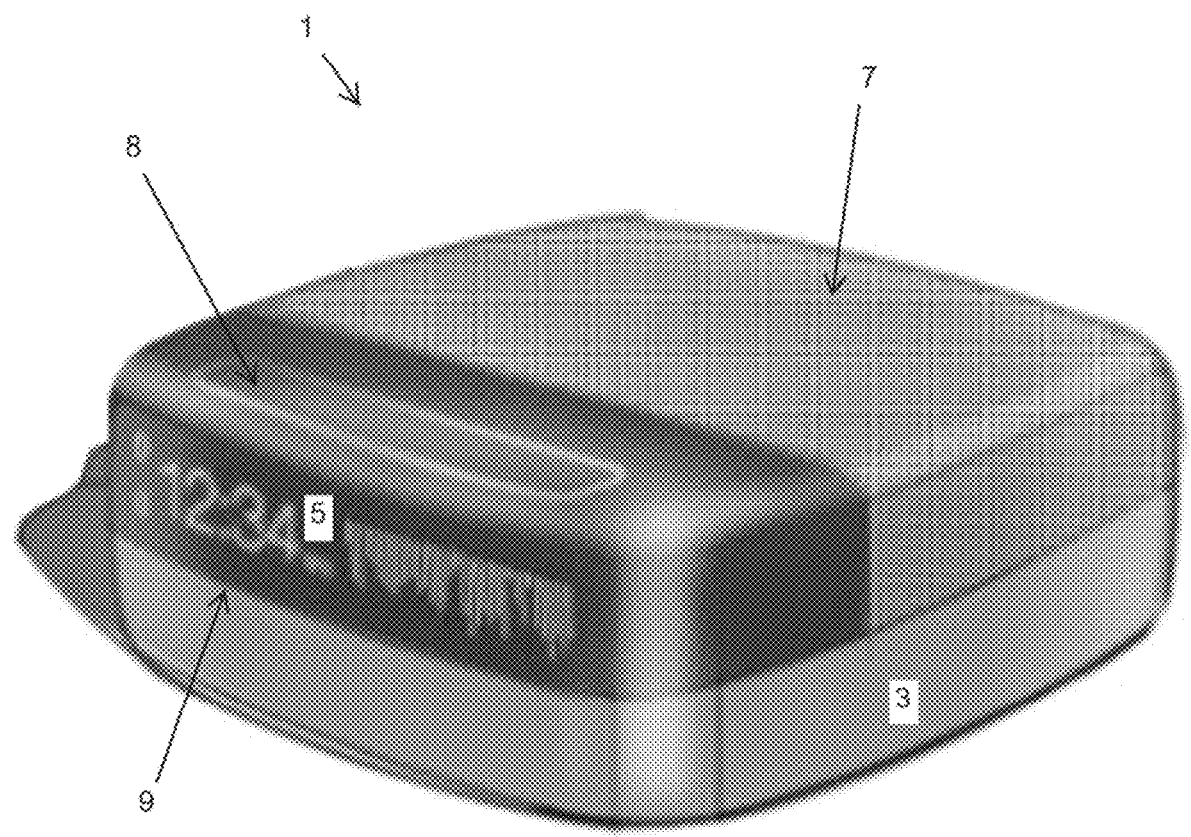
FIG. 1C is a front perspective view of a sleep quality scoring and improvement device with a square housing in one example of the present disclosure.

FIGS. 1A-1C are front perspective views of a sleep assistance device 1 in three examples of the present disclosure. As shown, a sleep assistance device 1 may include a housing 3, a display screen 5, speakers 7, and buttons 8 or a touchscreen 9 for inputting information into the sleep assistance device. A wide variety of forms may be utilized for a sleep assistance device, including a rectangular shape (e.g. FIG. 1A), an elongate cylindrical tower (e.g. FIG. 1B), or a flat square shape (e.g. FIG. 1C). However, as one of ordinary skill in the art will appreciate, any suitable form factor may be utilized that may be suitable for being placed nearby a user while sleeping, such as on a night stand, for example. In such examples, housing 3 may be formed into a suitable shape from any rigid materials, including plastics, metals, wood, or composites.

In some examples, display screen 5 may provide biometric or sleep information gathered by sleep assistance device 1 that may be of interest to a user. Such information may include information regarding the user's biometrics observed during sleep periods, such as information regarding the user's presence, heart rate, heart rate variability, respiratory rate, ambient temperature, movement, snoring, or sleep state over time. This may be direct information or derived information. In some examples, display screen 5 may also include a clock as shown in FIGS. 1A-1C.

Speakers 7 may comprise any suitable speaker system for generating sounds, as may be familiar to one of ordinary skill in the art. In some examples, speakers 7 may comprise an upwards firing driver along with an acoustic deflector, to provide an omni-directional acoustical experience. Such configurations may be helpful for providing non-directional, room-filling sounds for a soundscape or a white noise while a user is sleeping. Omni-directional sounds systems may be particularly helpful to achieve soothing sounds, a natural wake-up experience, and a consistent listening experience throughout the room. As one of ordinary skill in the art will appreciate, any acceptable sound system for speakers 7 may be employed for producing room-filling sounds, however.

Touchscreen 9 or buttons 8 may comprise any suitable means for delivering inputs to sleep assistance device 1, including a tactile sensor coupled to a surface of housing 3 for detecting the presence of a user's fingers and for detecting pressure, such as when a virtual button on touchscreen 9 is being pressed by a user. Virtual buttons may be displayed on touchpad 9 in a manner familiar to one of ordinary skill in the art in order to allow an operating system to accept input commands from a user. In this manner, sleep assistance device 1 may be configured to accept input commands in a variety of ways and in a variety of contexts, by providing a programmable user interface that may present options and choices to a user via touchpad 9. In other examples, touchscreen 9 may present a permanent display of fixed virtual buttons or include fixed physical buttons 8 for receiving inputs from a user.

In some examples, display screen 5 and a touchscreen 9 may not be necessary or may be reduced in function because a user's smartphone or other external computing device may be used for linking with sleep assistance device 1, displaying information from sleep assistance device 1, accepting inputs, and delivering them to sleep assistance device 1 in order to control its functions. In such a configuration, the display screen 5 and touchscreen 9, if any, may display and control only typical bedside clock-related functions, such as time, alarm, and music selection, or a simplified component of the sleep score, such as just a total score value, may be displayed.

Figure 2:
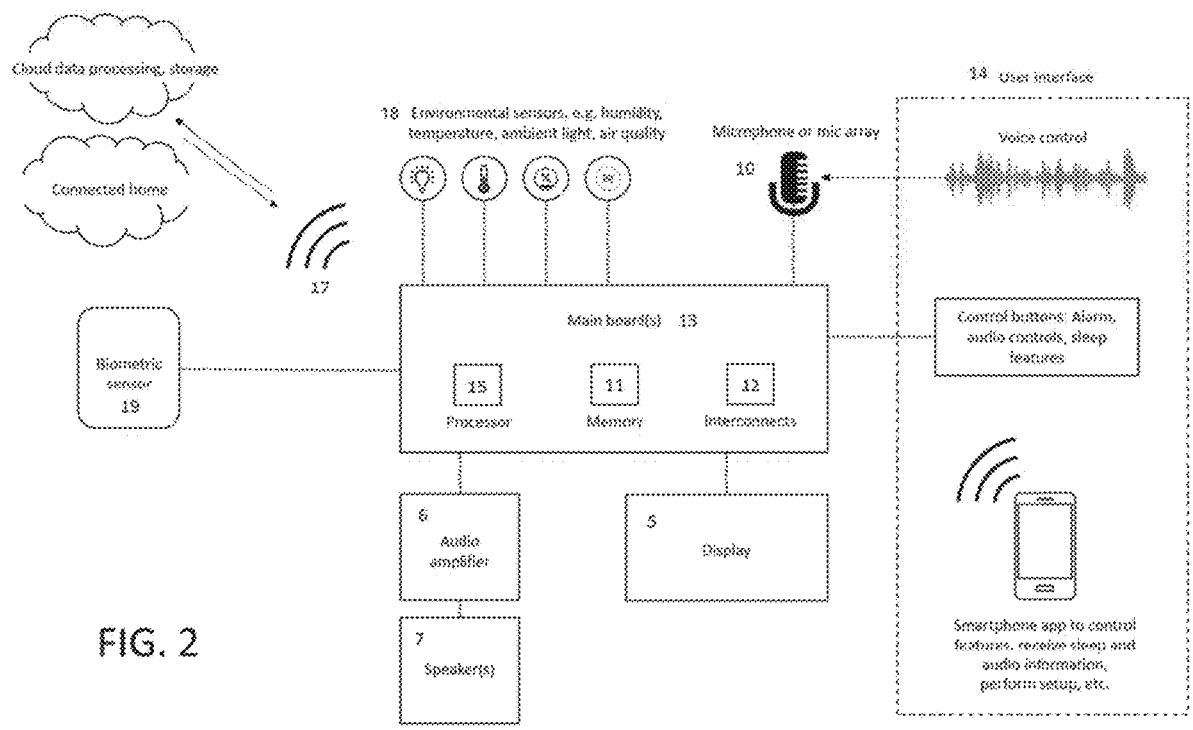
FIG. 2 is a schematic of the components of a sleep assistance device in one example of the present disclosure.

FIG. 2 provides an exemplary schematic of a sleep assistance device, showing its components. As shown, sleep assistance device 1 may include one or more main board(s) 13, including a processor 15, memory 11, and interconnects 12. Main board 13 controls the operation of several other connected components, such as a microphone 10, display screen 5, audio amplifier 6, speakers 7, and buttons 8 or a touchscreen 9 for inputting information into the sleep assistance device. Communications hardware 17 may include any wired or wireless communication means suitable for use with a sleep assistance device, such as WiFi, Bluetooth, USB, micro USB, or any suitable wired or wireless communications technologies known to one of ordinary skill in the art. Main board 13 also receives information from biometric sensor 19 as well as any number of environmental sensors 18, for detecting environmental conditions, such as temperature, humidity, ambient light, and air quality. Main board 13 also receives inputs based on a user's interactions with a user interface 14, which may include voice-activated commands detected by microphone 10; various audio, alarm, and sleep control inputs received from buttons 8 or touchscreen 9; or inputs received from a companion application running on a user's smart phone or other external computing device. The communications hardware 17 may also provide communications with external data sources, such as weather reports, and connected home services providing access to such things as lights, thermostat, locks, and any of the sensors 18.

Microphone 10 may be any suitable microphone for detecting and sampling sounds within a user's bedroom or sleep space, as is known to one of ordinary skill in the art. In some examples, microphone 10 may be an arrayed microphone that is suitable for distinguishing between sounds produced by sleep assistance device 1 and sounds produced externally within the user's bedroom or sleep space. In examples where microphone 10 comprises an arrayed microphone, it may comprise a plurality of omnidirectional microphones, directional microphones, or any mixture thereof, distributed about sleep assistance device 1. Microphone 10 may be coupled to processor 15 for simultaneous processing of the signals from each individual microphone in a manner familiar to one of ordinary skill in the art in order to distinguish between sounds produced by sleep assistance device 1 and other sounds within the room and to analyze any external noises for use with sound-masking subroutine 27, as discussed below. Microphone 10 may employ beamforming or other techniques to achieve directionality in a particular direction, for example, towards a sound to be analyzed. Microphone 10 may be employed both for monitoring the user's sleep and for receiving spoken user interface commands.

Biometric sensor 19 remotely detects information about a nearby user, including bed presence, respiration rate, heart rate, heart rate variability, or a sleep state among other biometric indicators. In some examples, biometric sensor 19 may be a contactless biometric sensor which may use an RF sensor for directing RF signals towards a user, measuring the strength of the backscattered signal, and analyzing the backscattered signal to determine the state of various vital signs of a user over time. Other contactless biometric techniques may include lasers for measuring minor skin deflections caused by a user's heart rate, heart rate variability and blood pressure; or image-based monitoring systems, whereby skin deflections caused by heartbeats and blood pressure may be observed and analyzed over time through a camera. Biometric sensor 19 may be configured to report detected biometric information to processor 15 for storage in memory 11 and to be analyzed for use in the various subroutines described herein.

In other examples, sleep assistance device 1 may also employ a direct biometric sensor as is known to one of ordinary skill in the art. A direct biometric sensor may include probes or contact pads, that may be disposed on or under the user's body or within their mattress or sheets in order to mechanically detect biometric information, such as movement, respiration, heart rate, blood pressure, and temperature, among others. Such sensors may include accelerometers, other motion sensors, or mechanical sensors such as piezoelectric sensors or other vibration sensors. The biometric information detected by the probes may then be communicated to sleep assistance device 1 using a wired or wireless connection in a manner known to one of ordinary skill in the art. In some examples, a biometric sensor may be placed within earbuds worn by a user. Other implementations may combine both contactless and direct biometric sensors. Mechanical sensors that measure the body through an intervening medium, such as bedding, are included in the category of "contactless" biometric sensors.

Figure 3:
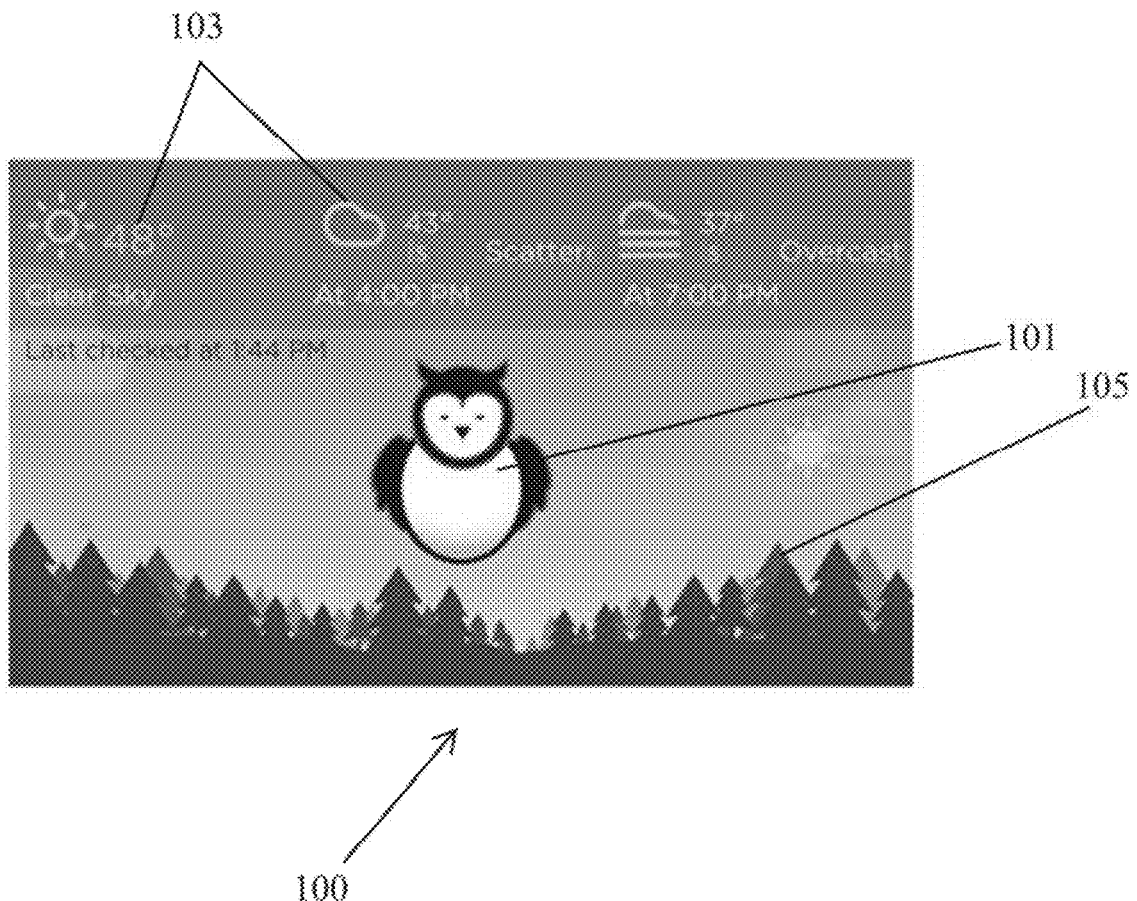
FIG. 3 is an example of home screen for a sleep assistance device.

Referring now to FIG. 3, an example of a home screen of a user interface of the present disclosure is shown. In some examples the user interface may be visible on the user interface screen 5 of the sleep assistance device. In other examples, the user interface may be visible on a screen of an external device, such as a cell phone, a tablet computer, a computer, or another electronic device through the use of an application for communicating with and/or controlling sleep assistance device 1.

The user interface may include a single home screen 100 providing information regarding sleep assistance device 1 or additional information regarding environmental conditions or the time of day, for example. The user interface may provide options or selections for a user to control sleep assistance device 1 based on the preferences of a user via a plurality of user menus. Where there is a plurality of user menus, home screen 100 may further include navigation icons that a user can select to switch the home screen displayed to another available menu.

Home screen 100 may include health indicia 101 corresponding in real-time to the output data from biometric sensor(s) 19. The health indicia 101 can represent a user's heartbeat or a user's respiratory rate, among any other available biometric information. Health indicia may be provided through any suitable visual representations of health and may comprise images that are not intuitively related to the associated biometric information. For example, in FIG. 3, health indicia 101 is shown in the form of an owl. In some examples, the owl's chest may be animated so that it expands and contracts at a rate that matches the user's detected respiration rate in order to provide a readily apparent depiction of the user's respiration which may be easily observed by a user. In other examples, the health indicia 101 can show a heart or other animated indicia that "beats" or glows at a rate that matches the user's heartbeat, as measured by the biometric sensor(s), in a similar manner.

In some examples, home screen 100 shows weather indicia 103 that correspond to current weather conditions and forecasted weather events. Such information may be gathered by sleep assistance device 1 from publicly available databases in a manner familiar to one of ordinary skill in the art and as disclosed, for example, in U.S. patent application Ser. No. 15/267,552 (incorporated by reference above).

In other examples, home screen 100 may also include landscape graphics 105 that reflect a soundscape selected by a user. For example, relaxation sounds may be part of a soundscape representing a collection of sounds corresponding to a location, such as a forest, a beach, a city street, or rain. As shown in FIG. 3, the landscape 105 may be a forest scene, for visual consistency with a forest scene soundscape has been selected by a user. In another example, when a beach soundscape is selected, landscape graphics 105 may change into a beach scene and health indicia 101 may likewise be switched to a seagull or other beach-related character. In this manner, menu 100 provides health indicia 101 and landscape graphics 105 that can match the context of any relaxation and noise-masking sounds selected by a user.

Figure 4A:
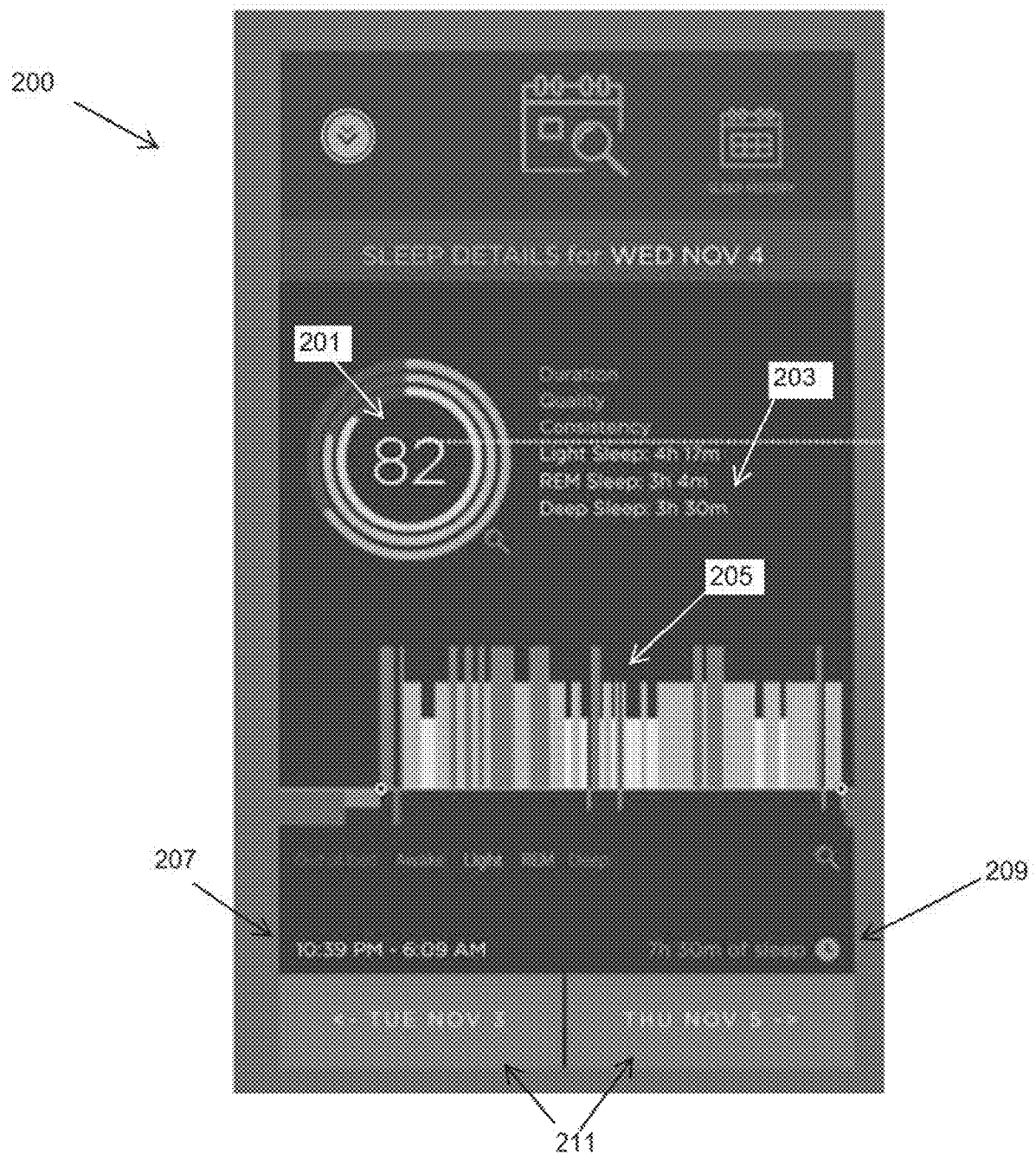
FIG. 4A is a sleep details report in one example of the present disclosure.

FIG. 4A is an example of a sleep details report that may be provided in one example of the present disclosure. In some examples, the sleep assistance system may provide a sleep score for a user based on observations received from biometric sensor 19 and other inputs, as disclosed, for example, in U.S. patent application Ser. No. 15/267,464 (incorporated by reference above). For example, once a sleep session has concluded, the system may generate a sleep details report 200 that may be viewable on an external computing device or user interface screen 5. As shown, a sleep details report may provide a graphical sleep score 201, depicting the overall quality of a user's sleep on that date, as observed by biometric sensor(s) 19 and recorded by the system. In some examples graphical sleep score 201 may have color-coded bars or rings representing sleep criteria, such as the duration of the sleep, the quality of the sleep, and the consistency of the sleep, which may all contribute to an overall sleep score. In this example, the actual colors used and are not shown; color is only used to help visually distinguish the bars or rings, and is redundant with their relative position. A numerical representation of an overall sleep score may also be provided with or without any color-coded bars. When available, sleep statistics 203 may also be displayed, such as the amount of light sleep, REM sleep, or deep sleep observed during the prior sleep session.

Sleep details report 200 may also include a hypnogram 205, which may provide another graphical depiction of the depth of a user's sleep throughout the night. In some examples hypnogram 205 may be presented by a time graph representing periods of absence, waking, light sleep, REM sleep, or deep sleep along an x-axis. Different heights along a y-axis may correspond to the relative depth of the sleep during that timeframe. Bars corresponding to different depths (or absence) of sleep may also be different colors, showing the same information in two different ways. In other examples, only one or the other of color and bar height may be used, or the two may convey different information. Sleep details report 200 may also include basic information regarding the sleep session, such as the sleep timeframe 207 or a sleep duration 209. Where available, buttons 211 may be used to view sleep details reports for other available days. In other examples, a user may select a date range encompassing a plurality of sleep sessions in order to view relevant sleep statistics within that range, such as the average sleep score, duration, or quality, among other statistics. For example, button 217 may allow users to view sleep details for a single day, whereas button 215 may allow users to see comparative sleep data over multiple days. The data may be available from the sleep system itself, stored in the device implementing the user interface, or retrieved on-demand from a networked resource.

Figure 4B:
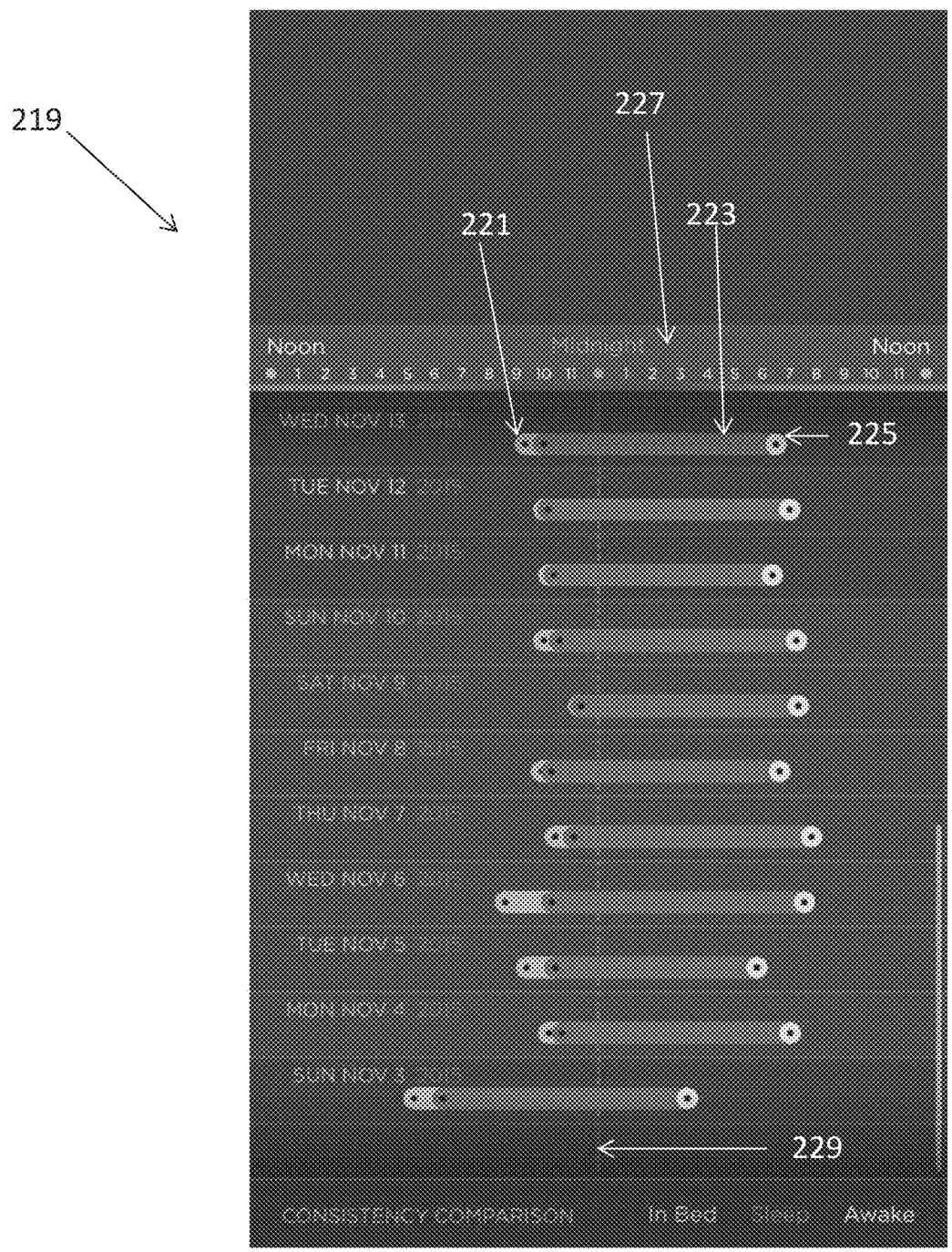
FIG. 4B is a sleep consistency report in on example of the present disclosure.

FIG. 4B shows an example of a sleep consistency report 219 in on example of the present disclosure that may be an example of a report spanning multiple days, which may be accessed by selecting button 215 in FIG. 4A, as previously discussed. In this example, a sleep consistency report 219 provides a graphical representation of a user's observed sleep patterns over multiple days. For example, each sleep session is depicted for multiple days in rows corresponding to separate dates. The sleep sessions are depicted as lines with multiple segments, including an in-bed segment 221 which corresponds to times where the user was detected as being in bed, a sleeping segment 223, which corresponds to times when a user was detected as being asleep, and an waking segment, 225, which corresponds to times when a user was detected as waking from sleep. In some examples, these line segments may be color-coded lines representing the duration of each sleep segment. In this example, the actual colors used and are not shown; color is only used to help visually distinguish the sleep segments, and is redundant with their relative position.

A horizontal time bar 227 may also be included within sleep consistency report 219 to depict the timeframe for any given sleep event or sleep segment within the consistency report. To aid the user in quickly assessing their sleep consistency across multiple days, a vertical time line 229 may also be depicted, which traverses the sleep segments and allows for visual comparison of a user's detected sleep state at the same time on multiple nights. In some implementations, the time line may be fixed at the middle of time bar 227 and the time line 229 may be moved by either dragging the time bar 227 to a desired position or touching a specific hour within the time bar.

Figure 5:
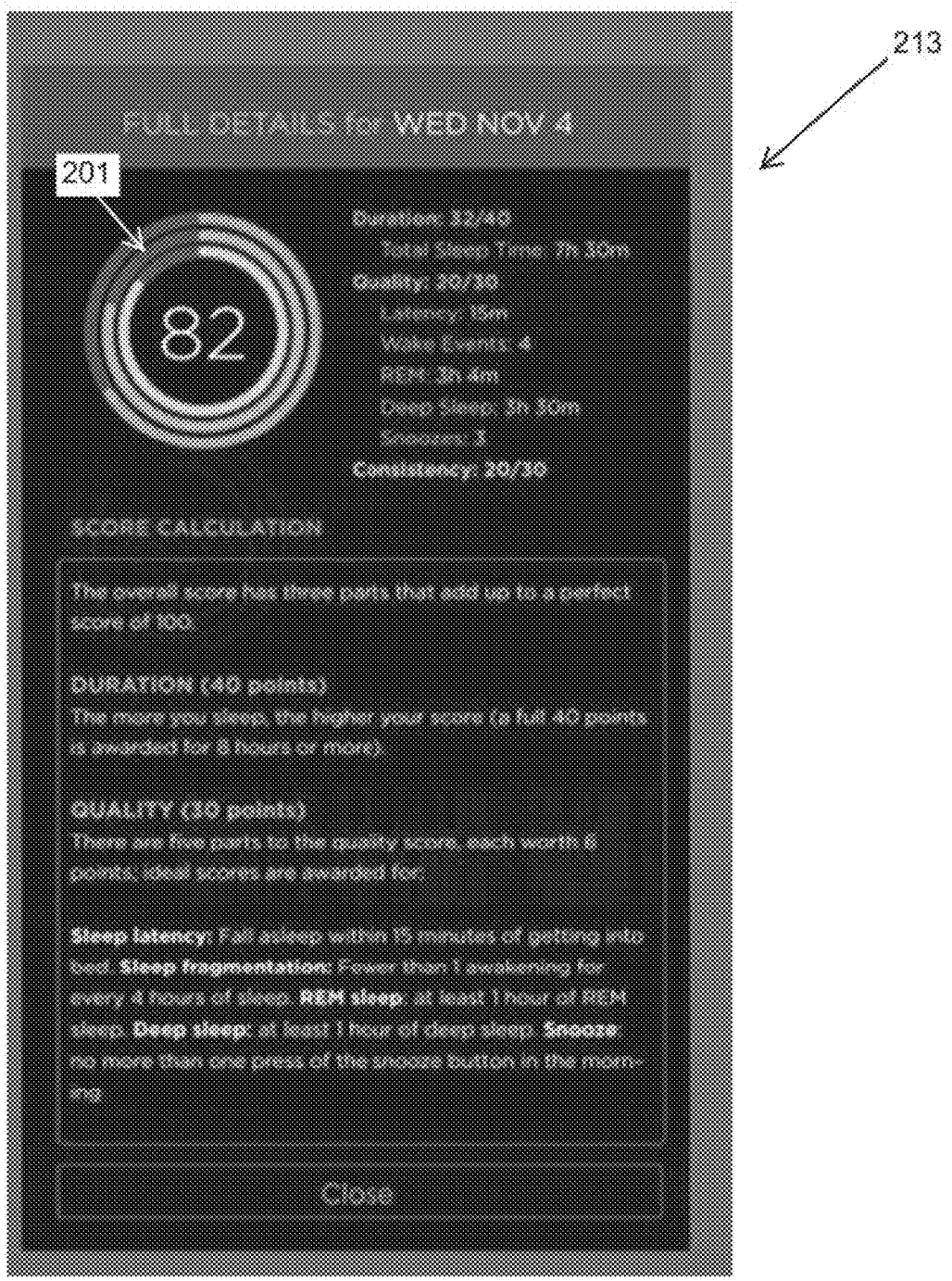
FIG. 5 is a full sleep details report in one example of the present disclosure.

In some examples, a user may activate a full details report 213, as shown in FIG. 5, by selecting a button or link within sleep details report 200. In some examples, graphical sleep score 201 may also serve as a virtual button for accessing a full details report 213. As shown in FIG. 5, full details report 213 may present a user with further details regarding the data and methodology supporting their sleep score for the selected sleep session. A sleep score may be based, in some examples, on three basic sleep criteria, including duration, quality, and consistency. Sleep duration may be a reflection of the detected duration of a user's sleep session, with a perfect score reserved for the upper limit of medically recommended amounts of sleep, which may be eight or nine hours or more. In some examples, a perfect score may be assigned 40 "points" towards a user's total sleep score. Sleep quality may be calculated based on several sub-factors, such as latency (e.g. the speed with which a user falls asleep), the number of observed waking events, the amount of observed REM sleep, the amount of observed deep sleep, or any observed mechanical interactions with sleep assistance device 1, such as snoozes. These factors may contribute to an overall sleep score using any suitable methodology for scoring and weighting these or any other relevant sleep quality criteria. In some examples, a perfect quality sleep may be assigned 30 "points" towards a user's total sleep score. Sleep consistency may also be scored based on the overall similarities between sleeping and waking times of a user or any other sleep factors which may be compared night-to-night, based on information stored in memory 11 or available to the system from an on-line resource. In some examples, an ideally consistent sleep pattern may yield 30 "points" towards a user's overall sleep score for a given session. While the present disclosure depicts sleep scoring based on the criteria of duration, quality, and consistency, any combinations of sleep criteria known to one of ordinary skill in the art may be evaluated to determine an overall sleep score. In such examples where a sleep score is calculated, the user interface further may include indicia indicating a user's sleep score in real-time.

Figure 6:
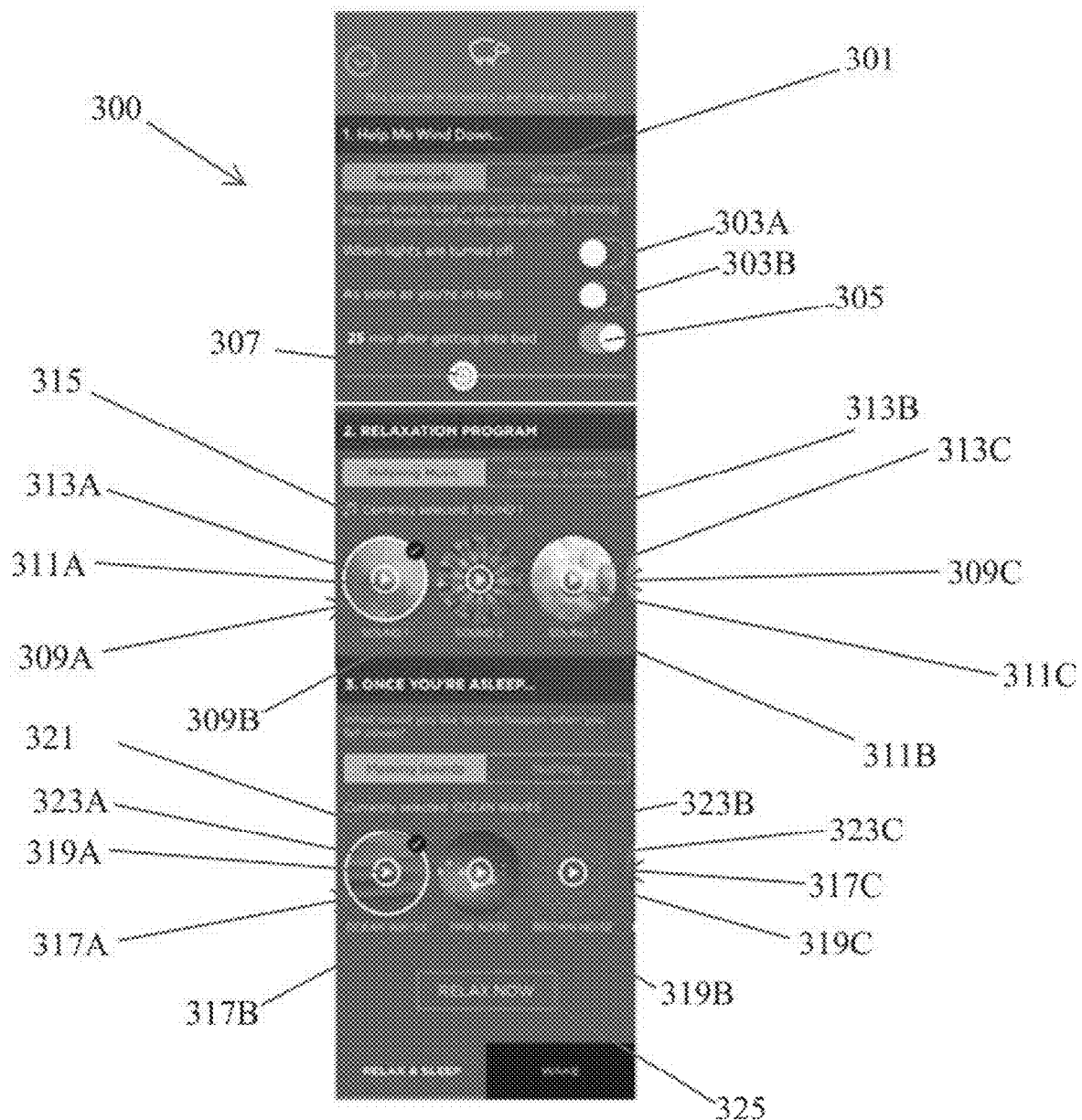
FIG. 6 is a sound selection menu in one example of the present disclosure.

FIG. 6 shows a sound selection menu 300 that may be presented in examples of the present disclosure for configuring a sleep assistance device throughout a sleep session. In some examples, sleep assistance device 1 may be configured to provide for relaxation sounds throughout a sleep session, including a relaxation period and an in-sleep or sound-masking period, as disclosed in in U.S. patent application Ser. No. 15/267,567 (incorporated by reference, above). Various options may be configured using a graphical user interface, including a button 301 for selecting whether to initiate a wind-down routine automatically or based on a manual initiation by a user. If automatic initiation is selected, additional options may be configured for establishing when a wind-down routine may be initiated. For example, buttons 303 may be utilized for selecting a triggering event. Any suitable triggering events may be defined within sound selection menu 300. For example, button 303A will instruct the system to initiate a wind-down routine upon detecting that the lights have been turned off. Button 303B may instruct the system to initiate a wind-down routine as soon as the user's presence is detected in bed by biometric sensor(s) 19. However, as one of ordinary skill in the art will appreciate, any number of detectable triggering events may be defined within the system and may be selected through buttons 303.

Button 305 and slider 307 may be used to set a delay in the initiation of a wind-down routine. For example, a user may wish to initiate a wind-down routine based on a preset delay after a triggering event has been detected. Such delays may be useful if a user wishes to read in bed, for example, before engaging in a wind-down routine. In those cases, button 305 may be provided to allow a user to select a delayed wind-down routine. Slider 307 may then be utilized to set the amount of the delay. In FIG. 6, for example, the delay has been set to 25 minutes after detecting a triggering event.

As also shown in FIG. 6, a sound selection menu 300 may also include a plurality of sound icons 309A-C for selecting the sounds played during a wind-down routine. Sound icons 309A-C may provide a visual indication as to the nature of the sound by including a visual representation of a particular sound within the icon. For example, if a user is assessing sounds for a forest soundscape, icons 309A-C may include an image of an owl or woodpecker, for example, to indicate that the icon relates to an owl or woodpecker sound element. In this manner, sound icons 309 may provide an intuitive indication of the associated sound element based on the image depicted within the sound icon, itself. In some examples, sound icons may further include preview buttons 311A-C which may be employed as shown in FIG. 6, for example. In some examples, a preview button may include a triangular icon indicating that the button may be pressed to play a sample of the associated sound. Preview buttons 311A-C may provide a selectable virtual button for previewing sounds for a user in order to determine whether the sounds should be included, excluded, or adjusted within a soundscape.

Sound icons 309A-C may also include an activation status icon 315. Activation status icon 315 provides another selectable button for allowing a user to either include or exclude a particular sound from a soundscape. In some examples, when a user clicks on an edge 313A of a sound icon 309A, an activation status icon 315A appears, showing that the user has selected that sound to be currently played. When a user clicks on the edge 313A of the sound icon 311A again, the activation icon 315A disappears, indicating that the user has not selected that sound element to be currently played or included within a soundscape during a relaxation routine. Any number of sound icons 309 may be made available to a user. In some examples a user may be able to swipe left or right in order to view additional sound icons 309, as shown for example in FIG. 6.

Sound selection menu 300 may also include a plurality of sound icons for selecting sounds or a soundscape during a sound-masking routine to be played once a user has fallen asleep. As shown in FIG. 6, a user may select which sound elements to include in a sound-masking routine through the use of sound icons 317A-C, which function in the same manner as sound icons 309A-C, described above. As with sound icons 309A-C, sound icons 317A-C may also include a visual indicator of the associated sound element, preview buttons 319A-C, and an activation status icon 321 located on the edge 323A-C of the sound icons. A virtual button 325 may also be provided to manually initiate a wind-down routine immediately.

Figure 7:
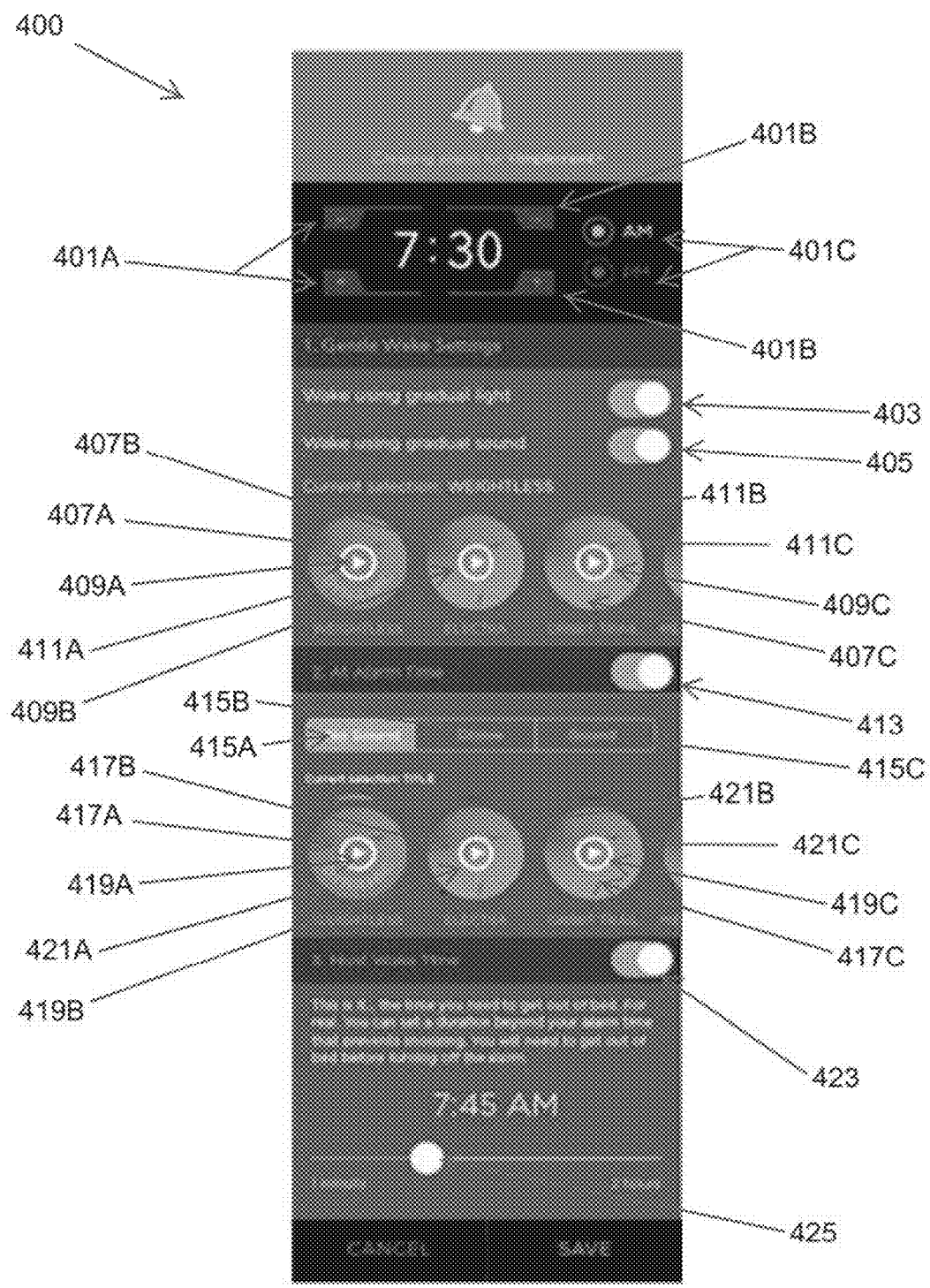
FIG. 7 is an alarm menu in one example of the present disclosure.

FIG. 7 shows an alarm menu 400 for configuring an intelligent wake-up system, such as the intelligent wake-up system disclosed in U.S. patent application Ser. No. 15/267,552 (incorporation by reference, above). Sound selection menu 400 may include a series of virtual buttons and sound icons for controlling an intelligent wake-up system in a gentle wake-up mode, at an alarm time, or at a must-wake time. For example, virtual buttons 401 may be used to set an initial wake-up time. Buttons 401A may be used to set the hour by increasing or decreasing the wake-up hour, as shown. Buttons 401B may be used to set the minute settings by increasing or decreasing the desired minute setting. Buttons 401C may be used to select either an AM or PM setting.

A user may also configure gentle wake settings using alarm menu 400. For example, virtual button 403 may be selected to configure the sleep assistance device to begin gradually increasing the light levels in the bedroom during a gentle wake-up routine. Virtual button 405 may be selected to configure the sleep assistance device to begin gradually increasing the volume of a wake-up sound or soundscape selected by a user, culminating in the ultimate wake-up volume at the user's predefined wake-up time.

If a gentle wake routine has been enabled, a user may further select which sound elements to include in a gentle wake-up routine through the use of sound icons 407A-C, which function in the same manner as sound icons 309A-C, as described above. As with sound icons 309A-C, sound icons 407A-C may also include a visual indicator of the associated sound element, preview buttons 409A-C, and an activation status icon (not shown in FIG. 7) located on the edge 411A-C of the sound icons. As with sound icons 309 and 317, additional sound icons 407 may be brought into view by swiping left or right in order to cycle through all of the available sound elements in menu 400.

A user may also configure separate alarm settings for the user-defined alarm time in alarm menu 400. For example, a user may activate or deactivate separate alarm settings by either selecting or de-selecting virtual button 413. When virtual button 413 is selected an alarm program will play the alarm based on the alarm time settings defined in alarm menu 400. If virtual button 413 is not selected, an alarm program will continue to play the sounds selected for the gentle wake routine upon attaining the preset wake-up time. If virtual button 413 is selected, buttons 415 may allow a user to select which type of alarm sounds to use in an alarm including a "No Sound" option (using virtual button 415A), which may be used, for example, when a user wishes to wake using lighting features, alone; a "Chime" option (using virtual button 415B); or a "Sound" option (using virtual button 415C).

If the "Sound" option is selected, a user may further select which sound elements to include in the alarm through the use of sound icons 417A-C, which function in the same manner as sound icons 309A-C, described above. As with sound icons 309A-C, sound icons 417A-C may also include a visual indicator of the associated sound element, preview buttons 419A-C, and an activation status icon (not shown in FIG. 7) located on the edge 421A-C of the sound icons. As with sound icons 309, 317, and 407, additional sound icons 417 may be brought into view by swiping left or right in order to cycle through all of the available sound elements.

A final wake up time may also be set in alarm menu 400. For example a user may activate or de-activate a final wake-up time functionality by selecting or de-selecting virtual button 423. Once selected, a snooze option may become unavailable at the specified final wake-up time and a wake-up sound will not be silenced until biometric sensor 19 detects that a user has actually vacated the bed. Slider 425 may allow a user to specify a final wake-up time. As shown in FIG. 7, in some examples, a final wake-up time may be configured with reference to the wake-up time previously set by a user. For example, slider 423 may indicate an amount of time after the initial wake-up time to allow a user to wake up normally. Once that time has passed, sleep assistance device 1 may enter a final wake-up mode in which a snooze option may be disabled, as described above.

Figure 8:
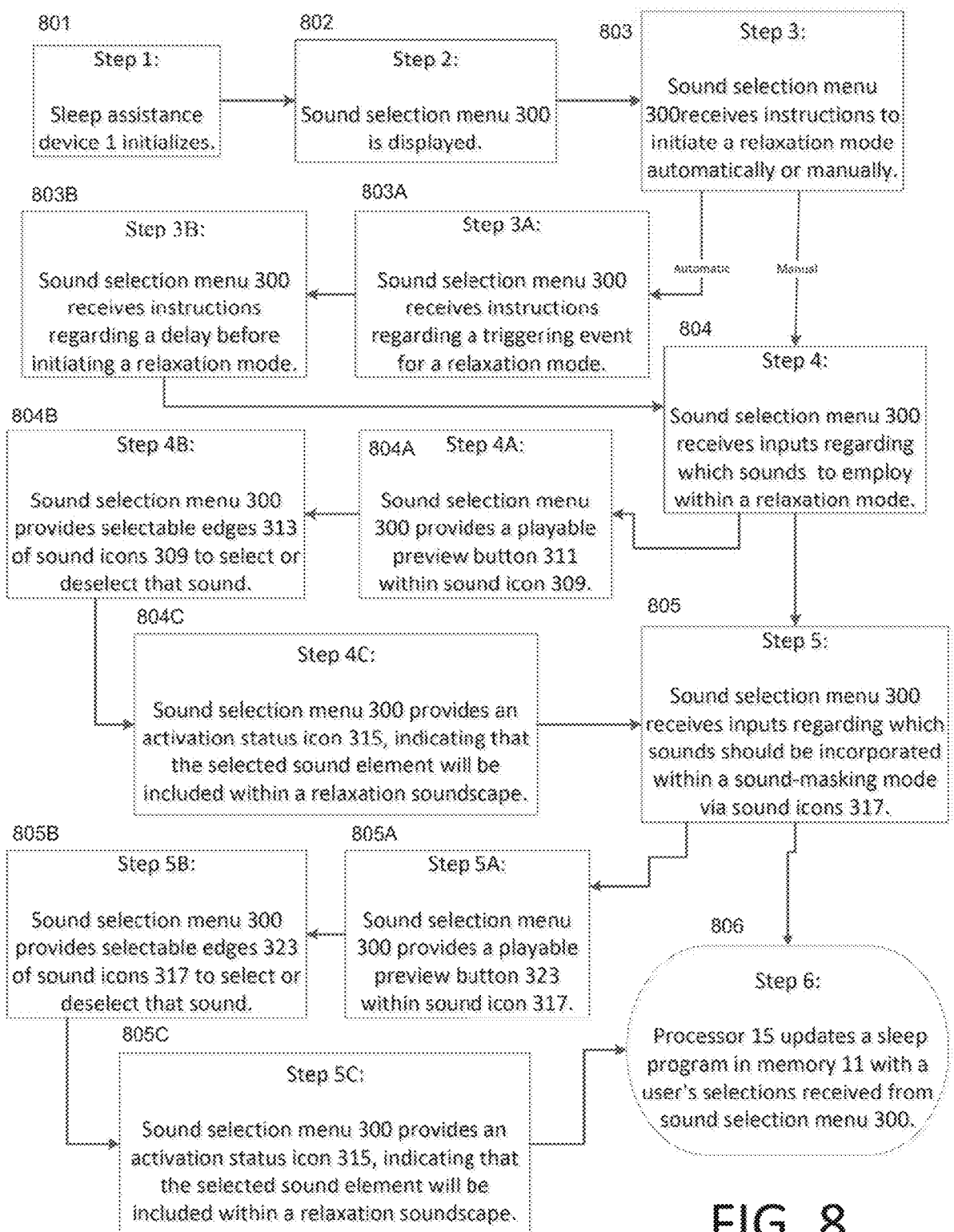
FIG. 8 is a flowchart showing a series of steps for a method for controlling a sleep program in one example of the present disclosure.

FIG. 8 shows a series of steps for a method for controlling a sleep program in one implementation of the present disclosure. At step 1, sleep assistance device 1 initializes, along with processor 15, memory 11, and user touchscreen 9 (box 801 in FIG. 8). At step 2, the system may display a sound selection menu 300, which may be presented to the user on an external computing device or on touchscreen 9 (box 802). Sound menu 300 may include a user interface with selectable virtual buttons for customizing a sound program. At step 3, to the user interface receive instructions via sound selection menu 300 as to whether a user wishes to automatically initiate the sound program in a relaxation mode or whether a relaxation mode should only be manually initiated via button 301 (box 803). If button 301 is selected, the system may receive inputs from a user regarding a triggering event for a relaxation mode in step 3A (box 803A). When button 303A is selected, a relaxation mode may be initiated when a user turns down their lights. When button 303B is selected, a relaxation mode may be initiated when a user gets into bed, for example. In step 3B, the user interface receives inputs from a user to set a delay for initiating a relaxation mode (box 303B). For example, a delay after a triggering event is detected may be set using selectable button 305 and slider 307 for setting the delay desired delay.

At step 4, to the user interface receive inputs regarding which sounds a user wishes to employ within a relaxation mode (box 804). For example, a sleep program may play relaxation sounds in a relaxation mode and sound-masking noises in a sound-masking mode. In some examples, the relaxation sounds may take the form of a soundscape including multiple, related sound elements playing to provide a realistic soundscape, such as a forest soundscape, a city street soundscape, or an ocean soundscape, for example. At step 4, to the user interface receive inputs regarding which sounds should or should not be incorporated within a relaxation sound using sound icons 309A-C. In step 4A, to the user interface provides preview buttons 311A-C within sound icons 309A-C for previewing a sound or a portion of a sound associated with the respective sound icon (box 804A). In step 4B, to the user interface provides selectable edges 313A-C of sound icons 309A-C to select or deselect that sound (box 804B). At step 4C, the user interface provides an activation status icon 315 located on one or more edges 313A-C of the sound icons 317A-C, indicating that the selected sound element will be included within a relaxation soundscape (box 804C).

At step 5, the user interface receives inputs regarding which sounds should or should not be incorporated within a sound-masking mode via sound icons 317A-C in sound selection menu 300 (box 805). In step 5A, to the user interface provides preview buttons 319A-C within sound icons 317A-C for previewing a sound or a portion of a sound associated with the respective sound icon (box 805A). In step 5B, the user interface to provide a selectable edge 323A-C of icons 317A-C to select or deselect a given sound (box 805B). At step 5C, to the user interface provides an activation status icon 321A located on the edges 323A-C of sound icons 317A-C, indicating that the selected sound element will be included within a sound-masking soundscape (box 805C).

At step 6, processor 15 receives the user's selections from sound selection menu 300 and updates a sleep program in memory 11 with a user's selections made within (box 806). Such selections may include the user-defined preferences for initiating the sound program as well as the user's sound element selections for inclusion in a relaxation soundscape or a sound-masking soundscape. If a user deselects a sound, processor 15 may remove the associated sound element from the list of sounds that the system mixes to create a soundscape in a relaxation mode or a sound-masking mode.

FIG. 9 shows a series of steps for a method for operating a home screen 100 on a sleep assistance device in one implementation of the present disclosure. At step 1, a processor 15; memory 11 in communication with the processor; an external computing device or display 9 in communication with the processor; and at least one biometric sensor 19 for sensing at least one of a heart rate, a respiratory rate, a presence of a user, or movement of a user are initialized (box 901 in FIG. 9). At step 2, processor 15 may be configured to read current biometric, environmental, and system conditions in order to gather information for presentation in menu 100 (box 902). At step 2A, processor 15 may be configured to read biometric information from biometric sensor 19 on a continual or periodic basis and record currently detected biometric conditions of a user within memory 11 with each reading (box 902A). At step 2B, processor 15 may be configured to gather environmental information (e.g. current and upcoming weather information, pollution information, pollen information, and/or traffic information) from sensors 8 or publicly available databases and to store the environmental information within memory 11 (box 902B). At step 2C, processor 15 may be configured to retrieve information regarding current system settings, such as whether the system is currently configured to play a sound program and, if so, what type of soundscape has been selected for playing by the user (box 902C).

At step 3, processor 15 provides information to a home screen 100 for displaying information regarding the current biometric, environmental, and system conditions to a user (box 903). For example, at step 3A, home screen 1000 provides a health indicia 101 corresponding to real-time biometric information detected by biometric sensor(s) 19 in one aspect of home screen 100 (box 903A). Home screen 101 may also animate the appearance of health indicia 101 based on biometric information received from biometric sensor(s) 19 and stored within memory 11. For example, health indicia 101 may be animated to appear to breath as a user is detected breathing or pulsate along with a user's detected heart rate. Health indicia 101 may further be animated to appear awake when a user is awake or asleep when a user is detected as sleeping.

At step 3B, home screen 100 displays landscape 105 reflecting a soundscape setting for sleep assistance device 1 (box 903B). For example, if a user has selected to play a forest-themed soundscape, then home screen 100 may display forest landscape 105. If an ocean soundscape has been selected by a user, then home screen 100 may display an ocean landscape 105. Any number of graphical scenes may be used to maintain a visual interface that reflects the currently selected soundscape. Note that the graphical scene may be quite abstract—a simple outline of a tree line, for example, to indicate a forest, or waves to indicate an ocean soundscape. In some examples health indicia 101 may also reflect the selected soundscape as well. For example, an owl may be displayed as health indicia 101 when a forest soundscape is selected, whereas a seagull may be selected when an ocean soundscape has been selected by a user.

At step 3C, home screen 100 may display weather indicia 103 or indicia of any other applicable environmental factors received by processor 15 (box 903C). For example, home screen 100 may display weather indicia sufficient to show the current or forecasted weather, including the temperature, the cloud cover, and precipitation. If traffic indicia are being provided, home screen 100 may display an indicator of the current traffic conditions along a pre-determined travel route. At step 4, processor 15 may be configured to continually check for updated information recorded in memory 11 regarding biometric, system, or environmental information and update the display within home screen 100 to reflect any new or updated information by returning to step 2 of the process (box 904).

FIG. 10 shows a series of steps for a method for controlling an intelligent alarm program in one implementation of the present disclosure. At step 1, sleep assistance device 1 initializes, along with processor 15, memory 11, user touchscreen 9 or an external computing device (box 1001 of FIG. 10). At step 2, an alarm menu 400 may be activated, which may be presented to the user on an external computing device or a touchscreen 9 (box 1002). Alarm menu 400 includes a user interface with selectable virtual buttons for customizing an intelligent wake-up program.

At step 3, alarm menu 400 receives inputs for setting a wake-up time for a user. For example, alarm menu 400 may be provided with buttons 401A-C for setting the hours, minutes, and an AM/PM settings for a wake-up time (box 1003). At step 4, alarm menu 400 may receive gradual wake-up settings through inputs within the menu (box 1004). For example, at step 4A, alarm menu 400 receives an indication that a user would like to use a gradual light feature within the intelligent alarm program for gradually raising the lighting with in the bedroom or sleep space through the selection of button 403 (box 1004A). At step 4B, alarm menu 400 receives an indication that a user would like to use a gradual sound feature within the intelligent alarm program for gradually raising the volume (or otherwise adjusting the acoustics) of the music or soundscape being played by sleep assistance device 1 through the selection of button 405 to gradually awaken a user from sleep (box 1004B). In step 4C, if the gradual sound feature is selected, alarm menu 400 receives information regarding which sound(s) should be played as part of a wake-up sound or soundscape during a the gradual wake-up through the use of sound icons 407A-C (box 1004C). As part of step 4C, alarm menu 400 provides preview buttons 409A-C within sound icons 407A-C for previewing a sound or a portion of a sound associated with the respective sound icon. Alarm menu 400 also provides a selectable edge 411A-C of a respective sound icon 407A-C to select or deselect that sound. Alarm menu 400 may also, as part of step 4C, provide an activation status icon located on the edge 411A-C of the sound icons 407A-C, indicating that the selected sound element will be included within the gentle wake-up feature.

At step 5, alarm menu 400 receives information regarding sounds that should be played when the wake-up time has been reached through inputs displayed on alarm menu 400 (box 1005). At step 5A, alarm menu 400 receives an indication that a user wishes to use sounds that are different from the gentle wake-up sounds once the wake-up time has been reached through a virtual button 413 (box 1005A). In examples where button 413 is not selected, the intelligent alarm program may continue using the sounds previously defined for the gentle wake-up mode once the wake-up time has been reached. In step 5B, if button 413 has been selected, alarm menu 400 may receive an indication as to what type of sound a user wishes to use once the wake-up time has been reached through virtual buttons 415A-B (box 1005B). For example, if no sound is desired, a user may select button 415A. If a chime is desired, a user may select button 415B. And if a soundscape is desired, a user may select button 415C. Of course, additional buttons 415 for any desired sound types may be displayed in step 5B in a manner familiar to one of ordinary skill in the art.

At step 5C, if "sounds" have been selected, alarm menu 400 may also receive an indication as to which sounds or sound elements should be included within a soundscape through sound icons 417A-C (box 1005C). As described above, sound icons 417A-C may include a visual indicator of the associated sound element, preview buttons 419A-C, and an activation status icon that may be located on the edge 421A-C of the sound icons when the sound is selected for inclusion within a soundscape. As with sound icons 309, 317, and 407, additional sound icons 417 may be brought into view by swiping left or right on touchscreen 9 in order to cycle through all of the available sound elements in alarm menu 400.

At step 6, alarm menu 400 may receive information regarding a "must-wake time" through inputs displayed on alarm menu 400 (box 1006). When a must-wake feature is activated, a sleep program may deactivate a snooze feature once the must-wake time has been reached. At step 6A, alarm menu 400 receives an indication as to whether a user wishes to use a must-wake feature by selecting a virtual button 423. If button 423 is not selected, then the alarm program will continue to function according to the settings defined for the wake-up time until the user has finally turned off the alarm without using a snooze feature. At step 6B, if button 423 has been selected, alarm menu 400 may also receive an indication as to how long to wait after the previously defined wake-up time to initiate must-wake feature using slider 425. For example, a user may set the wake-up time as 7:30 AM at step 3 and then set slider 425 to 15 minutes at step 6B to establish a must-wake time of 7:45 AM as shown, for example, in FIG. 7.

At step 7, processor 15 may be configured to accept the inputs received by alarm menu 400 and update the settings for an alarm program in memory 11 in order to configure an intelligent alarm to operate according to the settings defined by the user through alarm menu 400 (box 1007).

One of skill in the art will appreciate that the systems, methods and apparatuses outlined above may include various hardware and operating software, familiar to those of skill in the art, for running software programs as well as communicating with and operating any devices, including, for example, a biometric sensor, environmental sensors, a user interface, a computer network, a sound system, and any other internal or external devices. Such computerized systems may also include memory and storage media, and other internal and external components which may be used for carrying out the operations of this disclosure. Moreover, such computer systems may include one or more processors for processing and controlling the operation of the computer system, thus, embodying the processes of this disclosure. To that end, the processor, associated hardware and communications systems may carry out the various examples presented herein While the disclosed subject matter is described herein in terms of certain exemplary implementations, those skilled in the art will recognize that various modifications and improvements can be made to the disclosed subject matter without departing from the scope thereof. As such, the particular features claimed below and disclosed above can be combined with each other in other manners within the scope of the disclosed subject matter such that the disclosed subject matter should be recognized as also specifically directed to other implementations having any other possible permutations and combinations. It will be apparent to those skilled in the art that various modifications and variations can be made in the systems and methods of the disclosed subject matter without departing from the spirit or scope of the disclosed subject matter. Thus, it is intended that the disclosed subject matter include modifications and variations that are within the scope of the appended claims and their equivalents.

What is claimed:

1. An intelligent alarm comprising:
    a biometric sensor for sensing at least one of a heart rate, a respiratory rate, a presence of a user, or a movement of the user, the biometric sensor providing output data;
    a processor, memory in communication with the processor, a display in communication with the processor, and speakers in communication with said processor;
    said processor being configured to provide a user interface, wherein the user interface presents:
        selectable inputs for configuring a wake-up time;
        selectable inputs for configuring gentle wake-up settings including a first soundscape played during a gentle wake routine, said selectable inputs providing selectable sound indicia for selecting which sound elements of a plurality of sound elements are to be included in the first soundscape;
        selectable inputs for configuring alarm time settings;
        selectable inputs for configuring a must-wake time;
        a selectable input which provides for the user to select whether, at the wake-up time, the intelligent alarm continues to play the first soundscape played during the gentle wake routine as a wake-up sound, or whether the intelligent alarm plays at least one sound element different from the sound elements included in the first soundscape as the wake-up sound; and
        a selectable button for activating a must-wake time feature, whereby a snooze feature is deactivated upon reaching a must-wake time and the wake-up sound is silenced in response to a user movement sensed by the biometric sensor.

2. The intelligent alarm of claim 1, wherein said selectable inputs for configuring gentle wake-up settings further comprise:
    a selectable button for selecting a gradual sound feature.

3. The intelligent alarm of claim 1, wherein said inputs for configuring gentle wake-up settings further comprise a selectable button for selecting a gradual light feature.

4. The intelligent alarm of claim 1, wherein said selectable sound indicia further comprises:
    one or more selectable preview buttons for previewing the sound elements associated with the selectable sound indicia;
    one or more images related to the sound elements associated with the selectable sound indicia;
    one or more selectable edges for selecting the sound elements for inclusion within the first soundscape; and
    one or more activation status icons for indicating that the sound elements have been selected.

5. The intelligent alarm of claim 1, wherein said selectable inputs for configuring alarm time settings comprise:
    buttons for selecting the type of sound to be used as an alarm including at least one of a wake-up chime or a second soundscape; and
    selectable sound indicia for selecting sound elements to be included in the second soundscape.

6. The intelligent alarm of claim 5, wherein said selectable sound indicia further comprises:
    one or more selectable preview buttons for previewing the sound elements associated with the selectable sound indicia;
    one or more images related to the sound elements associated with the selectable sound indicia;
    one or more selectable edges for selecting the sound elements for inclusion within the second soundscape; and
    one or more activation status icons for indicating that the sound elements have been selected.

7. The intelligent alarm of claim 1, wherein said selectable inputs for configuring the must-wake time further comprise a slider for setting the must-wake time based on an amount of elapsed time after said wake-up time has passed.

8. The intelligent alarm of claim 1, wherein said selectable inputs are provided on an external computing device in communication with the processor.

\* \* \* \* \*